(12) United States Patent
Nallathambi et al.

(10) Patent No.: US 11,419,556 B2
(45) Date of Patent: Aug. 23, 2022

(54) METHOD AND SYSTEM FOR PACING PULSE DETECTION AND PACING ARTIFACT REJECTION

(71) Applicant: Vital Connect, Inc., San Jose, CA (US)

(72) Inventors: Gabriel Nallathambi, San Jose, CA (US); Nandakumar Selvaraj, San Jose, CA (US)

(73) Assignee: VITAL CONNECT, INC., San Jose, CA (US)

( * ) Notice: Subject to any disclaimer, the term of this patent is extended or adjusted under 35 U.S.C. 154(b) by 104 days.

(21) Appl. No.: 16/920,039

(22) Filed: Jul. 2, 2020

(65) Prior Publication Data

US 2022/0001184 A1 Jan. 6, 2022

(51) Int. Cl.
*A61B 5/00* (2006.01)
*A61N 1/37* (2006.01)
*A61N 1/365* (2006.01)

(52) U.S. Cl.
CPC ............ *A61B 5/7221* (2013.01); *A61B 5/721* (2013.01); *A61N 1/36585* (2013.01); *A61N 1/3706* (2013.01)

(58) Field of Classification Search
CPC .. A61B 5/7221; A61B 5/721; A61N 1/36585; A61N 1/3706
See application file for complete search history.

(56) References Cited

U.S. PATENT DOCUMENTS

| | | | |
|---|---|---|---|
| 10,595,776 B1 | 3/2020 | Selvaraj | |
| 2007/0265537 A1* | 11/2007 | Lee | A61B 5/333 |
| | | | 600/509 |
| 2008/0234591 A1* | 9/2008 | Scinicariello | A61N 1/375 |
| | | | 600/509 |
| 2015/0126822 A1 | 5/2015 | Chavin | |
| 2016/0331257 A1 | 11/2016 | Baumann et al. | |
| 2017/0347899 A1* | 12/2017 | Bhushan | A61B 5/02055 |
| 2018/0110419 A1* | 4/2018 | Volpe | A61B 5/1117 |
| 2018/0146874 A1* | 5/2018 | Walker | A61B 5/316 |
| 2018/0243578 A1 | 8/2018 | Volsosin | |
| 2019/0314192 A1 | 10/2019 | Milan | |

OTHER PUBLICATIONS

International Search Report and Written Opinion from International Application No. PCT/US2021/040109 dated Oct. 22, 2021, 7 pages.

* cited by examiner

*Primary Examiner* — Catherine M Voorhees
(74) *Attorney, Agent, or Firm* — Brundidge & Stanger, P.C.

(57) ABSTRACT

A method and system for detecting pacing pulses originating from implanted pacemaker using surface Electrocardiogram (ECG) signals measured at a relatively low sampling rate and also rejecting the pacing artifacts from the recorded surface ECG signals.

19 Claims, 14 Drawing Sheets

METHOD AND SYSTEM FOR PACING PULSE DETECTION AND PACING ARTIFACT REJECTION

BACKGROUND

An artificial pacemaker is a small medical device implanted usually in the chest or abdomen with one or more electrodes placed in one or more heart chambers due to common cardiac conditions including abnormal heart rhythms or arrhythmias such as bradycardia and heart failure. The sensing unit of a pacemaker comprising of electrodes senses the normal or abnormal electrical activity of heart and when the heart's natural impulse generator or pacemaker skips or fails, the pulse generator unit of the artificial pacemaker sends electrical impulses to the heart and regulate the heart's electrical conduction system, mechanical pumping and heart rate on a demand basis.

Detection of pacing pulses originating from implanted pacemaker using surface level Electrocardiogram (ECG) enables cardiologists to identify pacemaker driven rhythms and evaluate the functioning of the implanted pacemaker device in patients requiring such cardiac assist device leading to the determination regarding reprogramming of the pacemaker device for optimal treatment or pacemaker battery replacement.

Bed-side ECG monitors or portable Holter ECG monitors are commonly used to place ECG electrodes on chest and/or limbs, attached to the monitor via wires, and record/display ECG waveforms and simultaneous pacemaker pulses non-invasively. As typical pacemaker pulse durations are in the order of μs to few ms that requires high precision with a sampling frequency such as 4 kHz to reliably capture high frequency content of pacing pulses and display precisely using high bandwidth bed-side ECG monitors. Such bed-side ECG monitors are designed to capture surface ECG and pacemaker pulses mostly in a stationary condition (tethered to hospital bed) for a very limited time duration.

On the other hand, Holter ECG recorders can be set to operate at high sampling frequency and allow collecting of surface multi-lead ECG and pacer pulse signals in ambulatory conditions at home for 24-48 hours. Holter monitors are typically used to record surface ECGs and analyzed offline using proprietary software tools for to evaluate ECG morphological features and cardiac rhythms leading to deciding on the patient needs a pacemaker to restore regular cardiac rhythms. Holter recording in patients implanted with pacemaker can capture pacer pulses in addition to ECG signals when higher sampling rate is chosen. However, Holter recorders present limitations including no real-time monitoring by physicians, returning of the Holter recorder to doctor office for offline analysis, extended waiting period to obtain the summary results, and limited capabilities related to pacer detection and pacemaker diagnostic evaluation.

Such traditional bed-side ECG monitors and Holter recorders are furthermore not suitable for continuous, long-term and real-time monitoring and management of pacemaker implanted patients in their free-living home conditions. Due to lack of unobtrusive convenient wearable ECG sensor device for long-term monitoring, the pacemaker implanted patients may not get periodic assessments on the functioning of the pacemaker or implanted cardiac assist device that may have profound psychological implications including a perception to believe that the pacemaker device is functioning correctly. Thus, an unobtrusive wearable ECG monitor with real-time long-term continuous monitoring of pacemaker pulse recognition could be very valuable in assessing the functionality of implanted pacemaker and progression of treatment for cardiac conditions.

The long-term wearable ECG sensor devices usually have a sampling frequency of less than 1000 Hz, which is sufficient to capture predominant frequencies of interest corresponding to the ECG. But such low sample rate in wearable ECG sensor device is insufficient to reliably acquire and display the pacemaker pulses in the order of μs to few ms as opposed to the high bandwidth ECG systems with a relatively higher sampling frequency of approximately 4 kHz. Thus, wearable low bandwidth ECG systems with low sampling frequency are inherently not designed to capture the pacemaker pulses and may sporadically capture one or more samples of the pacing pulses depending on the selection of operational settings of the implanted pacemaker.

The present application overcomes the limitation of traditional ECG monitors for continuous unobtrusive ambulatory monitoring of pacemaker patients in their free-living conditions using a wearable ECG sensor device operating at a low sample rate. The present disclosure first describes the identification of the location of pacing pulses using a wearable ECG sensor device and sends out pacer detection output markers at a low sampling frequency (for example, 125 Hz). Accordingly, the pacer detection method and low-bandwidth wearable ECG sensor utilizes one or more surface ECG measured in implanted pacemaker patients to transform into a sensor output indicating presence or absence of pacer pulses at ECG sample level or cardiac cycle/beat level.

In traditional ECG monitors with high sample rate, the entire pacemaker pulses along with ECG can be captured by analog-to-digital converter (ADC) and the digital output signal includes an ECG signal and the concurrent incidences of pacemaker pulses intact. On the other hand, low bandwidth detecting wearable ECG sensor devices are not capable of capturing entire pacemaker pulses but sporadically capture one or more samples of pacer pulses in each cardiac cycle due to the inherent low sampling rate. Thus, the captured sporadic pacemaker pulse samples may result to appear as low-to-high amplitude artifacts along with ripples/distortions in the output ECG trace that may complicate deriving any clinical inferences with the output ECG trace. Therefore, the present disclosure also describes the pacer artifact rejection from the output ECG waveforms at a low sampling rate. Accordingly, the pacer rejection method processes one or more surface ECG and body acceleration measurements of low-bandwidth wearable ECG sensor device in implanted pacemaker patients to reject pacer artifacts and distortions from the ECG and provide a sensor output to indicate rejection of pacer pulses at ECG sample level or cardiac cycle/beat level bases.

Accurate assessment of pacemaker function or malfunction is essential to make clinical interpretations on pacemaker therapy and patient symptoms. The present disclosure also describes a wearable ECG sensor device with pacer detection and artifact rejection functionalities applied for the evaluation of the functioning of pacemaker device in a long-term continuous monitoring in ambulatory and free-living conditions in overcoming the limitations of the traditional ECG monitors. Accordingly, fusion of pacer detection outputs and pacemaker artifact rejected ECG outputs is used to determine the functional characterization of the pacemaker including pacer mode, pacer rate, pacer timing, pacing incidence, effective and ineffective pacing or pacer malfunction.

SUMMARY

In one example embodiment, a method to assess pacemaker modes and function, including: measuring, by a wearable sensor, an analog electrocardiogram (ECG) signal; measuring, by the wearable sensor, an analog accelerometer (ACC) signal; processing, by the wearable sensor, the analog ECG signal in a first channel and providing a first channel output; processing, by the wearable sensor, the analog ECG signal and the ACC signal in a second channel and providing a second channel output; and assessing, by the wearable sensor, a mode and function of a pacemaker device using correspondence measures between the first channel output and the second channel output.

In another example embodiment, a wireless sensor to assess pacemaker modes and function, including: measuring, by an electrode, an analog electrocardiogram (ECG) signal; measuring, by an accelerometer sensor, an analog accelerometer (ACC) signal; processing, by a processor, the analog ECG signal in a first channel and providing a first channel output; processing, by the processor, the analog ECG signal and the ACC signal in a second channel and providing a second channel output; and assessing, by the processor, a mode and function of a pacemaker device using correspondence measures between the first channel output and the second channel output.

In yet another example embodiment, a non-transitory computer-readable medium, associated with a wireless sensor to assess pacemaker modes and function, storing instructions that, when executed, cause one or more processors to perform operations comprising: measuring an analog electrocardiogram (ECG) signal; measuring an analog accelerometer (ACC) signal; processing the analog ECG signal in a first channel and providing a first channel output; processing the analog ECG signal and the ACC signal in a second channel and providing a second channel output; and assessing a mode and function of a pacemaker device using correspondence measures between the first channel output and the second channel output.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the brief description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
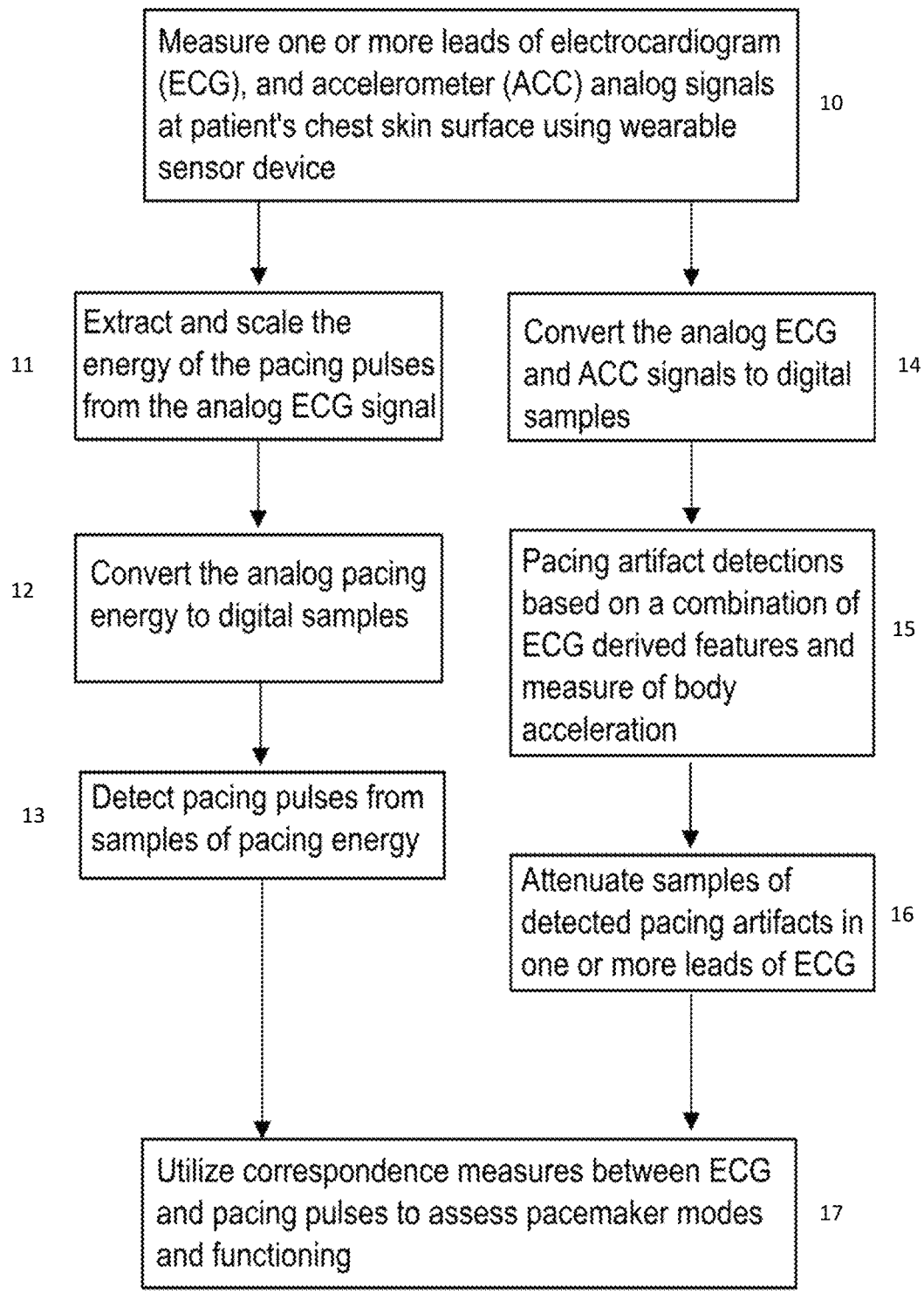
FIG. 1 shows an example block diagram for implementing one or more embodiments of pacing pulse indication.

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

FIG. 1 shows an example block diagram for implementing one or more embodiments of the system and method for pacing pulse indication at low sampling frequency, removing pacing artifacts, and evaluation of functioning of pacemaker. Accordingly, a wearable sensor is used to measure an electrocardiogram (ECG), and accelerometer (ACC) signals at patient's chest skin surface on the body at 10. The analog surface ECG is simultaneously processed in two separate channels. In channel A, the energy of the pacing pulses is extracted using filters tuned to capture spectral content outside ECG frequencies of interest and the energy of pacing signal is scaled in time at 11. The scaled pacing signal is then sampled with the analog to digital converter (ADC) at a low sampling frequency (for example, 125 Hz) at 12. Pacing pulses are detected from the digital Channel A signal at 13. In channel B, the analog surface ECG is sampled with the ADC at the same sampling frequency as Channel A (for example, 125 Hz), or in a similar range of sampling frequency. Likewise, accelerometer signals also are digitally converted in Channel B at 14. The pacing artifacts are detected in one or more independent leads of digital ECG based on features extracted from each lead of ECG data. The pacing detections of individual leads is aggregated and the presence or absence of pacing artifact is determined based on a measure of body acceleration derived from the digital accelerometer data at 15. Whenever the pacing artifact is detected in Channel B, its samples are attenuated in one or more ECG leads at 16. The mode and proper functioning of the pacemaker device is assessed using correspondence measures between the outputs of channel A and B at 17.

Figure 2:
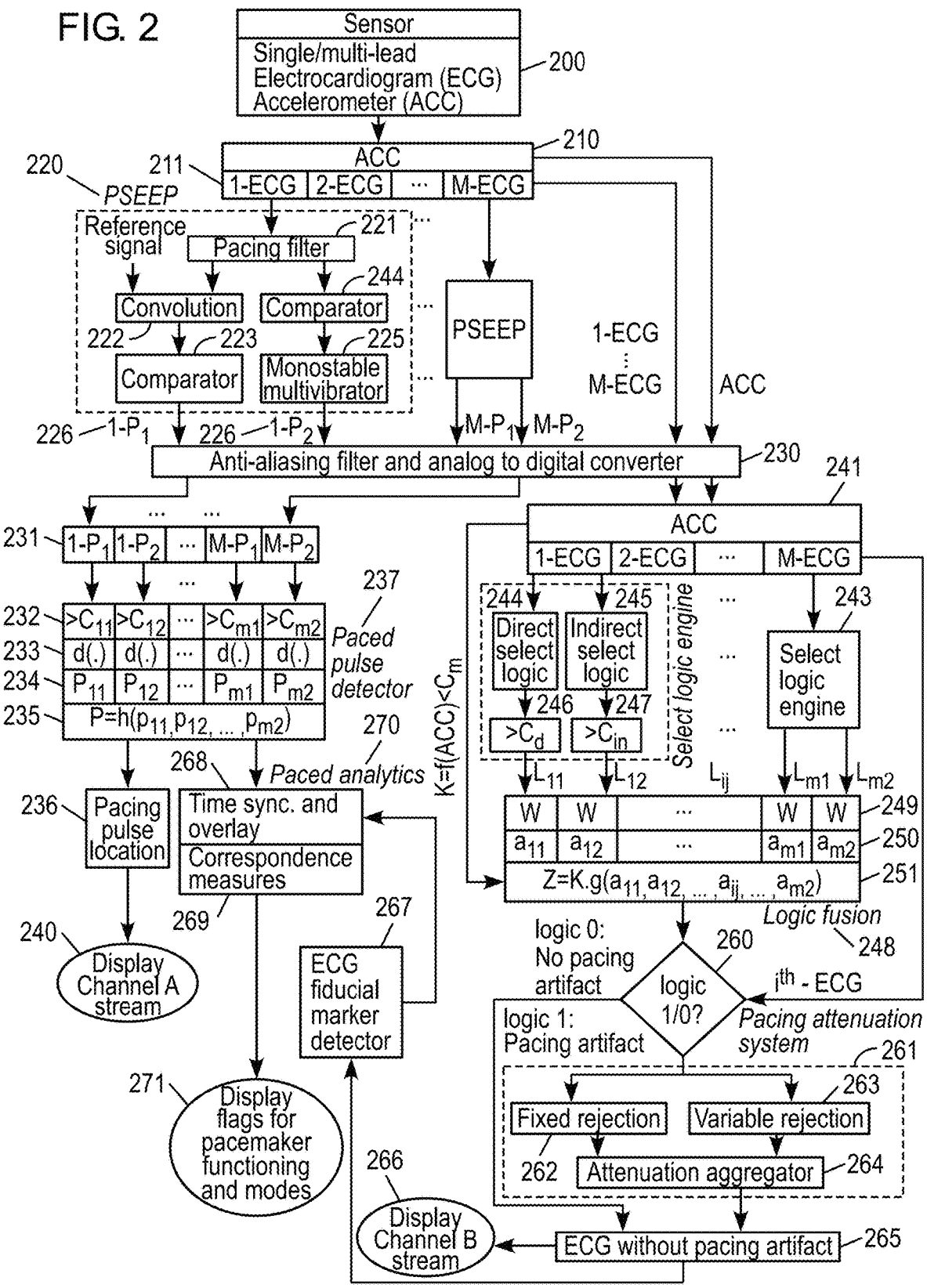
FIG. 2 shows an example block diagram for implementing pacing pulse indication algorithm.
Figure 3A:
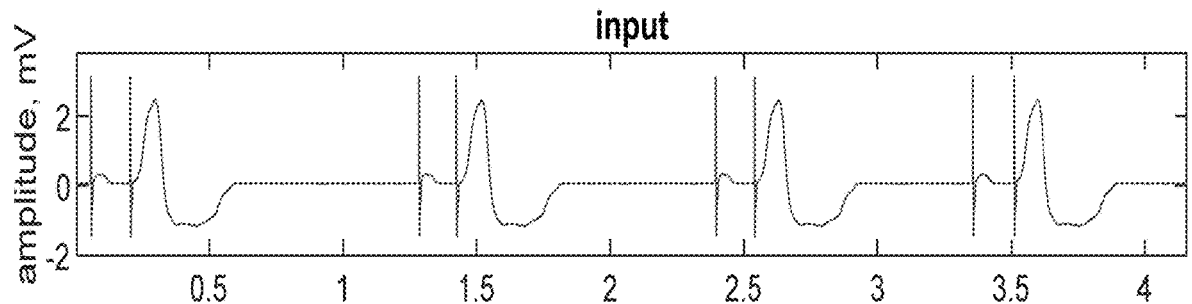
FIGS. 3A-3D shows example illustrations of output of the pacing filter.
Figure 3B:
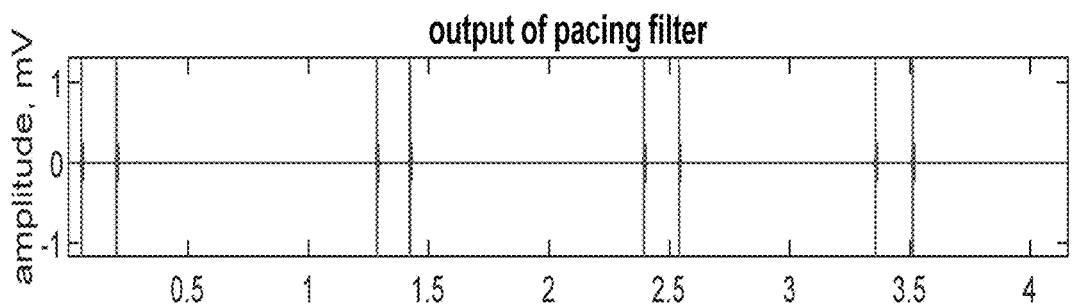

FIG. 2 shows additional details of the FIG. 1 system and method for indication of pacing pulses and removal of pacing artifacts from ECG by a block diagram. The sensor system may include single-lead or multi-lead ECG electrodes, and uni-axial or multi-axial accelerometer sensors. The form factor of wearable sensor device such as adhesive patch sensor, chest-band, or an electronic module adhered to body are within the scope of this invention. Further, in Channel A in a Paced signal energy extractor and processor (PSEEP) 220, the pacing energy corresponding to pacemaker pulses is extracted, and scaled in time. The analog ECG signals from one or more leads 211 is fed to the pacing filter 221 to extract the energy of the pacing signals from ECG 200. The pacing filter is an analog high pass filter or band pass filter, whose cut-off frequencies are outside the spectral content of the ECG signal. FIG. 3 shows an output of the pacing filter. Illustrations of the output of the pacing filter are provided in FIGS. 3A-3D. FIG. 3A shows an example of analog ECG with dual chamber pacing. FIG. 3B shows the extraction of significant portion of spectral components of pacemaker pulses and the removal of spectral components of ECG such as P wave, QRS complex, and T wave by the pacing filter.

Figure 3C:
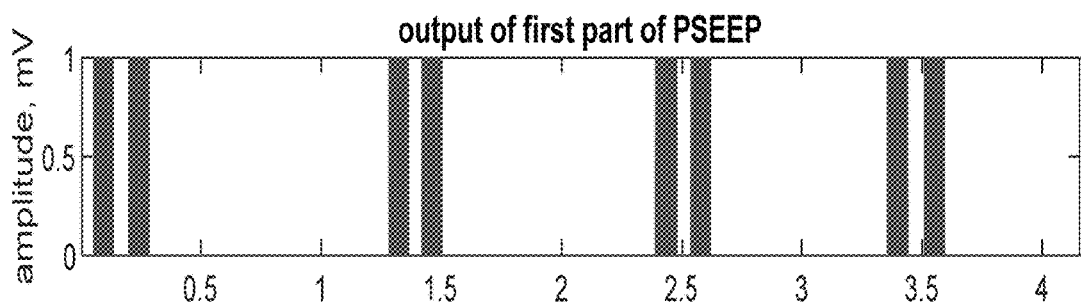
Figure 3D:
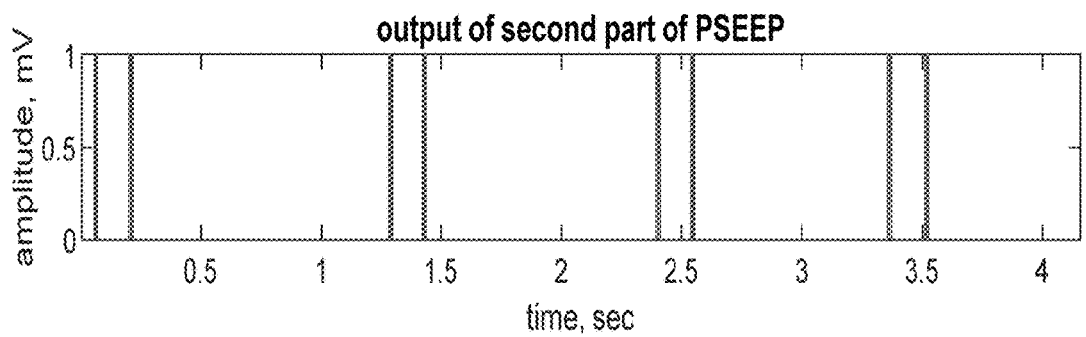

The output of the pacing filter is processed in two parts. In the first part, the pacing filtered signal is convolved with a reference signal in a convolution process at 222. The reference signals such as sinusoidal signal, step function, ramp function, parabolic signal, signum function, exponential signal, triangular signal, sinc function, linear or non-linear combination of the aforementioned basic signals are within the scope of the invention. The parameters of the reference signal such as amplitude and duration determines the time-scaling of the pulses at the output of the pacing filter. The convolved output is compared against a threshold to yield M–$P_1$, which is the output of first part of PSEEP due to the $M^{th}$-lead of the ECG, at Comparator 223. In FIG. 3C, an illustration of the output of first part of PSEEP is provided with the reference signal being a sinusoidal signal, and shows the processing and scaling of the energy of the pacing signal. In the second part, the pacing filtered signal is compared against a threshold by Comparator 224 and fed to the monostable multivibrator at 225 that is triggered based on the output of the comparator 224. Then, the monostable multivibrator 225 generates a pulse of pre-defined duration to yield M–$P_2$, which is the output of second part of PSEEP due to the $M^{th}$-lead of the ECG. The value of the threshold may be fixed, programmed based on pacemaker settings or learned from data. FIG. 3D shows the processing and scaling of the energy of pacing signal by the second part of PSEEP.

Figure 4A:
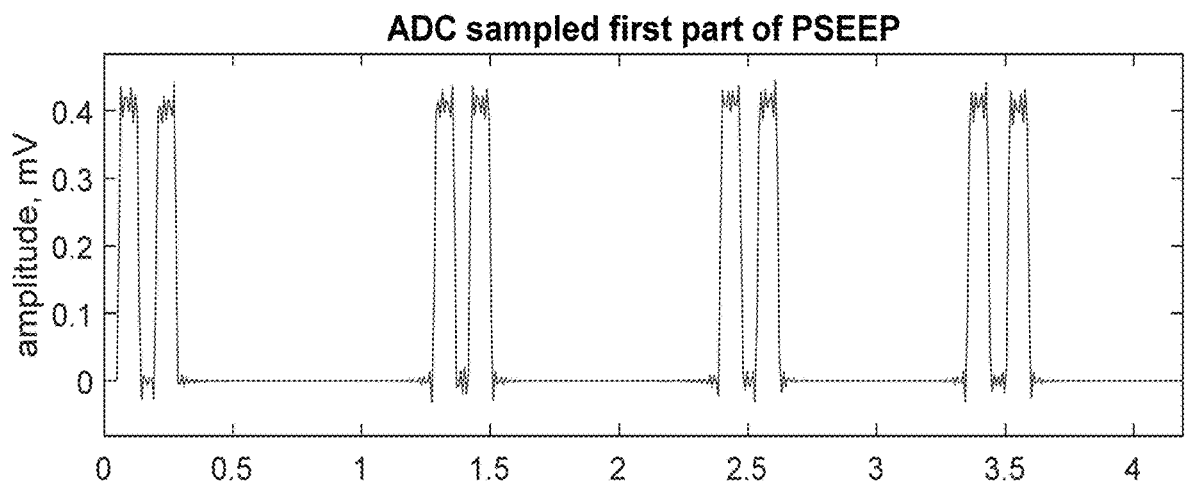
FIGS. 4A and 4B shows example illustrations of the output after the transformation of outputs of PSEEP by anti-aliasing filter and ADC, and shows the capture of the scaled pacemaker energy even at a low sampling frequency.
Figure 4B:
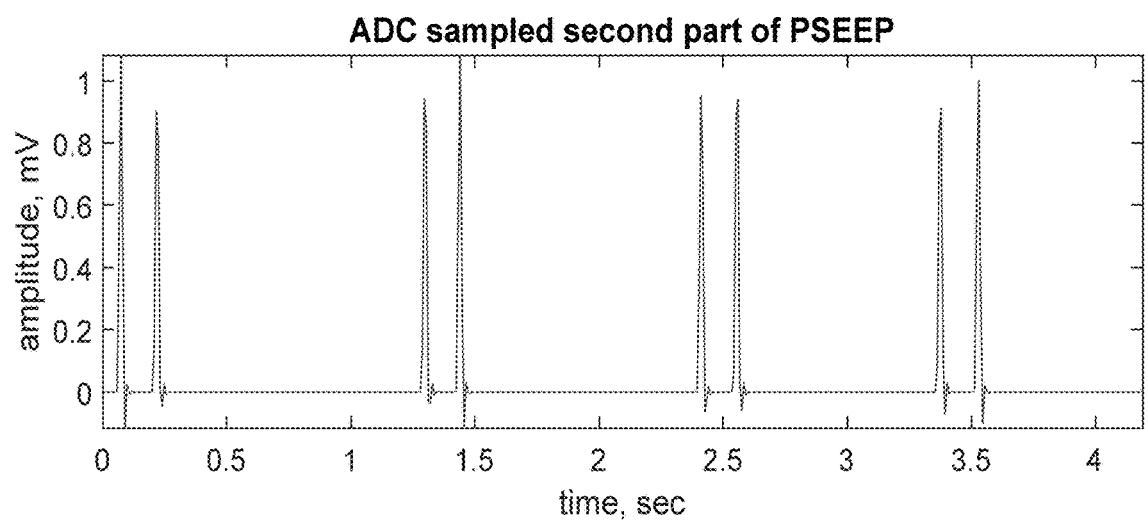

The analog signal streams 1–$P_1$, 1–$P_2$, . . . , M–$P_1$, M–$P_2$, collectively 226, are fed to anti-aliasing filter and converted to digital streams using an ADC operating at low sampling frequency (for example, 125 Hz) at 230. FIG. 4 shows the output after the transformation of outputs of PSEEP by anti-aliasing filter and ADC 239, and shows the capture of the scaled pacemaker energy even at a low sampling frequency of 125 Hz.

Figure 5A:
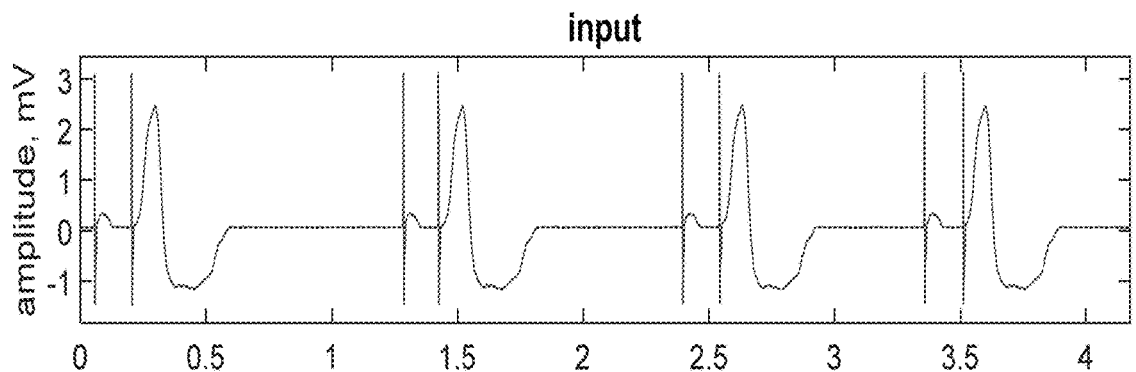
FIGS. 5A-5C shows example illustrations of the detection of pacing locations from the first and second part of PSEEP corresponding to one of the ECG leads in Channel A.
Figure 5B:
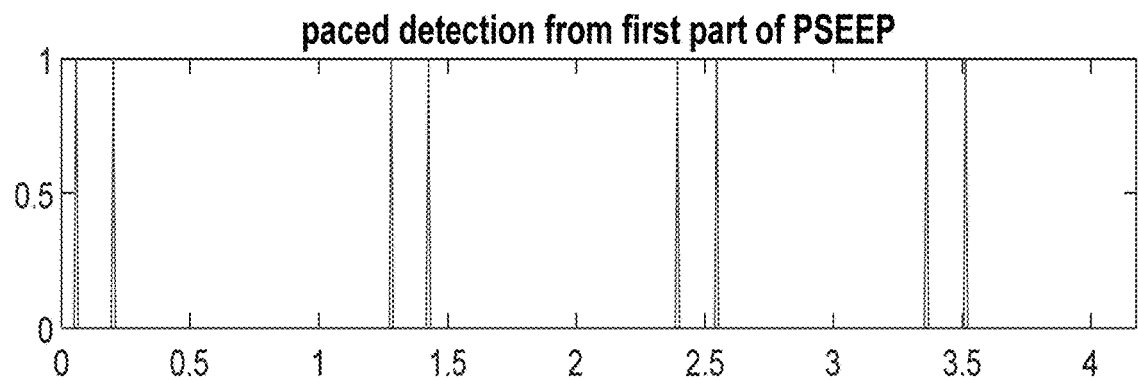
Figure 5C:
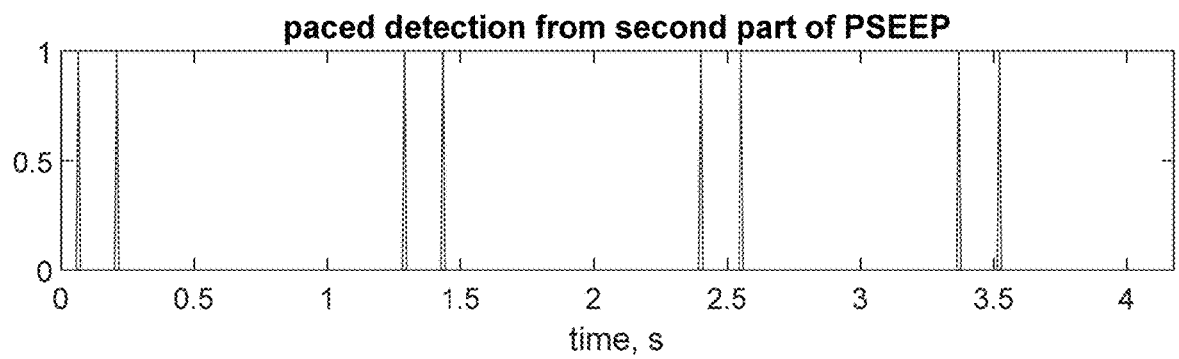

FIG. 2 further shows Paced pulse detector 237. As a first step towards finding the location of pacemaker pulses, the digital streams 1–$P_1$, 1–$P_2$, . . . , M–$P_1$, M–$P_2$ 231 are compared against thresholds $C_{11}$, $C_{12}$, . . . , $C_{m1}$, $C_{m2}$ at 232. The values of all the thresholds $C_{11}$, $C_{12}$, . . . , $C_{m1}$, $C_{m2}$ at 232 may be same or different, and is selected based on the sampling frequency. The output of the comparator is then fed to differentiator d(.) at 233 and compared to zero to obtain the location of pacing pulses $p_{11}$, $p_{12}$, . . . $p_{m1}$, $p_{m2}$ at 234 for each digital stream. An illustration of the detection of pacing location from first and second part of PSEEP corresponding to one of the ECG leads is shown in FIG. 5.

The final location of the pacemaker pulses is obtained by applying data fusion rules on $p_{ij}$ i.e., h($p_{11}$, . . . , $p_{ij}$, . . . , $p_{m2}$)∈(0,1) at 235 where logic 1 or logic 0 indicate the presence or absence of pacemaker pulses respectively. As an example, the data fusion rule h($p_{11}$, . . . , $p_{ij}$, . . . , $p_{m2}$) 235 to determine the location of pacemaker pulses 236 may be voting schemes such as majority voting, and threshold crossing (p out of 2m), combination of logical function rules such as AND, OR, etc., and Bayesian detection rules. Thus, the presence or absence of pacemaker pulses and their corresponding locations is detected and displayed in the processing of Channel A data stream at 240.

Figure 6:
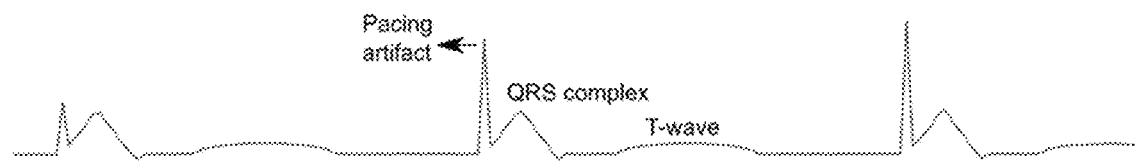
FIG. 6 shows an example illustration a pacing artifact and a single chamber paced ECG signal.

FIG. 2 also shows, in channel B, accelerometer signals also are digitally converted in Channel B. Likewise, the analog surface ECG from one or more leads 1-ECG, 2-ECG, . . . , M-ECG at 210 are fed to anti-aliasing filter and converted to digital streams using an ADC operating at the same low sampling frequency as in Channel 1 (for example, 125 Hz) at 230. At such low sampling frequencies, the pacemaker pulses are not represented and sporadically one or more samples of the pacing pulses may appear as artifacts on the ECG trace. In FIG. 6, an example of single chamber paced ECG signal sampled at 125 Hz is shown. An incidence of few samples of pacing artifacts is clearly observed. In the subsequent sections, schemes for reducing the incidence of such artifacts are provided.

Each of the M channels of digital ECG signals 241 is fed into the select logic engine 242, 243 to identify the samples that correspond to pacing artifacts. The select logic engine 242 relies on two channels of morphological ECG features namely direct select logic 244 and indirect select logic 245 to identify samples corresponding to pacing artifacts. The output of these single channels are employed independently to determine the pacing artifacts. Then the single channel detections are aggregated to obtain the final sample locations of the pacing artifact.

Figure 7:
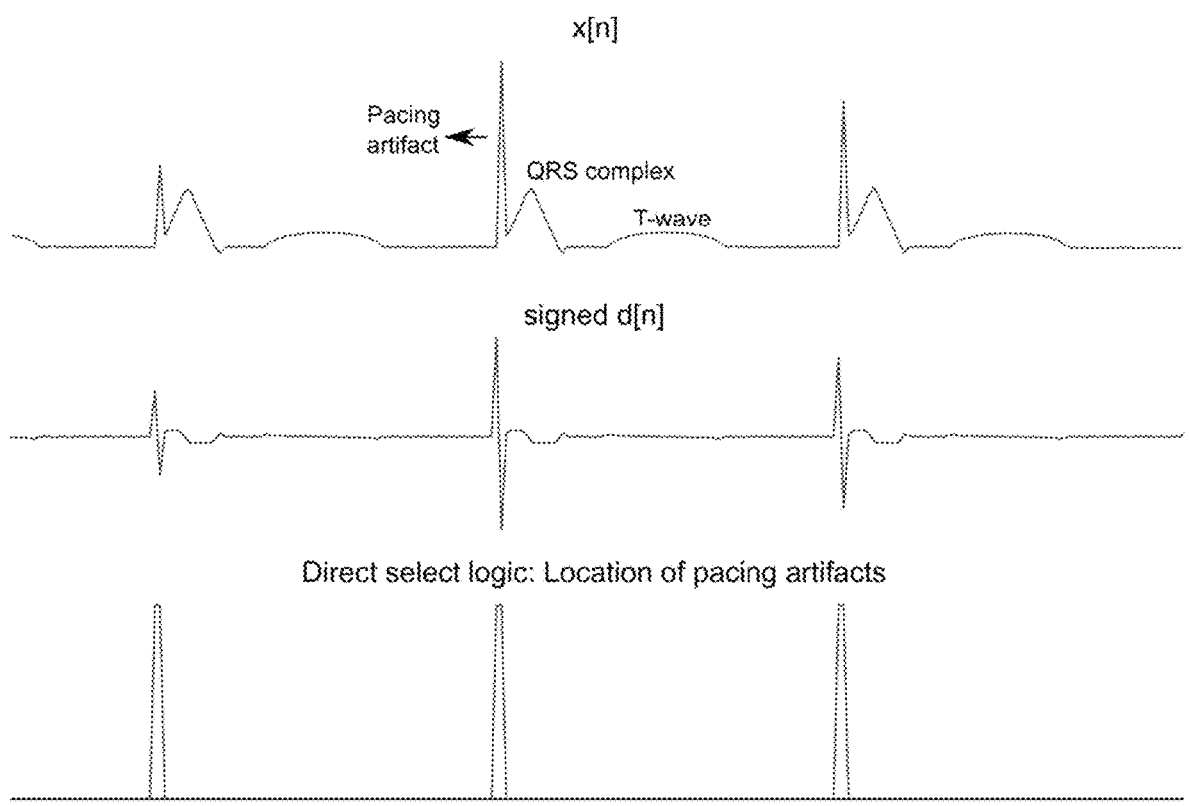
FIG. 7 shows example illustrations of the direct select logic.

Direct select logic 244 involves determining the presence or absence of pacing artifacts directly using the samples of each lead of ECG. An example of direct select logic is given by computing the absolute value of successive differences of the lead of ECG signal $x_i[n]$ as $d_i[n]=|x_i[n]-x_i[n-1]|$. Then $d_i[n]$ is compared against the threshold $C_d$ at 246, and samples of $d_i[n]$ that exceed the $C_d$ provide the location of the pacing artifact. This is illustrated in FIG. 7, where the location of pacing artifact is given by the digital stream of 1's and 0's depending on the presence or absence of pacing artifact as determined by the direct select logic scheme.

Figure 8:
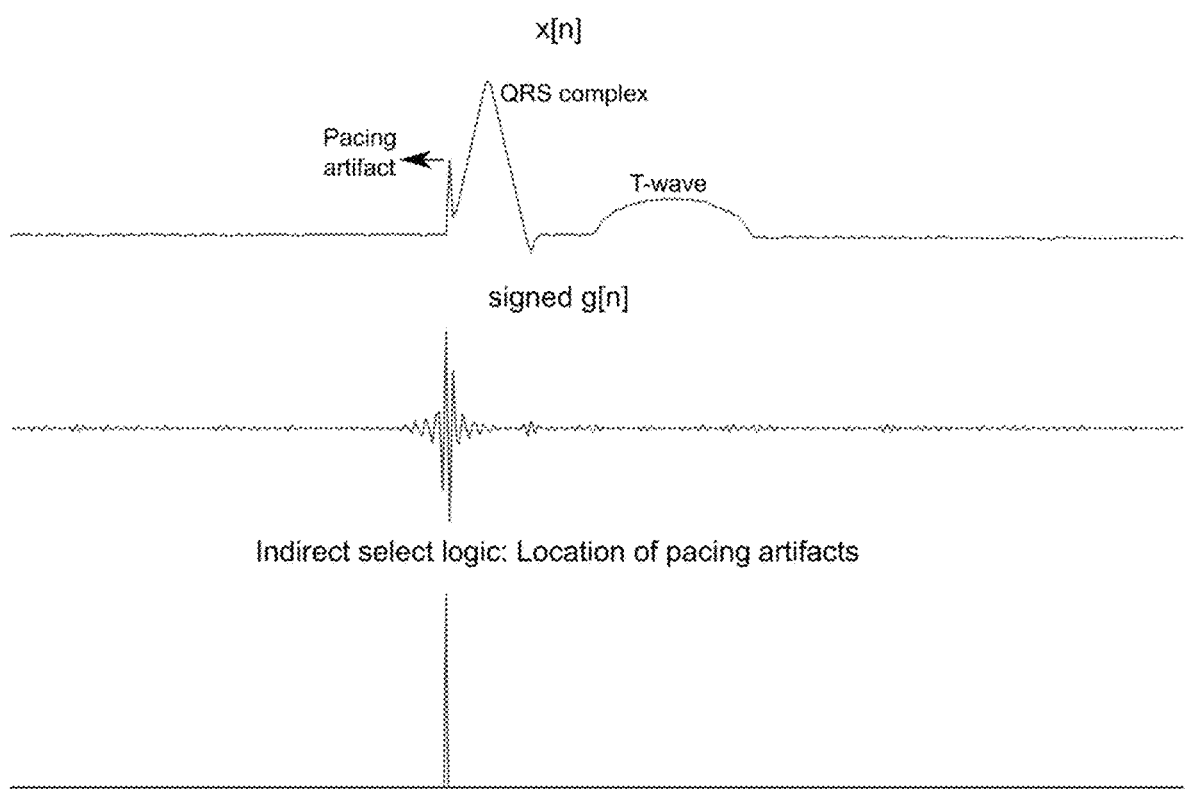
FIG. 8 shows example illustrations of the indirect select logic.

Indirect select logic 245 involves determining the presence or absence of pacing artifacts by signal manipulation operations performed on data in each lead of ECG signal. As an example, band pass filter or high pass filter is applied to extract fundamental pacing frequencies and remove the spectral features of the ECG signals. Let this filtered signal be $f_i[n]$. Computing the absolute value of successive differences of the $i^{th}$ lead of filtered signal $f_i[n]$ yields $g_i[n]=|f_i[n]-f_i[n-1]|$. Then the samples of $g_i[n]$ that exceed the threshold $C_{in}$ at 247 provide the location of the pacing artifact. This is illustrated in FIG. 8, where the location of pacing artifact is given by the digital stream of 1's and 0's depending on the presence or absence of pacing artifact as determined by the indirect select logic scheme.

The logical outputs of the select logic engine for each lead of ECG is fed to the logic fusion 248 for reliable determination of the presence or absence of the pacing artifact. Non-overlapping timing windows W at 249 of fixed duration is applied on the logical outputs of the select logic engine, $L_{ij}$. If the logical output $L_{ij}$ of the lead with $j^{th}$ select logic (j=1 for direct select logic, j=2 for indirect select logic) is 1 within W, then that window is assigned logic 1 i.e., when $L_{ij}=1$ within W, then the assigned value $a_{ij}=1$, and when $L_{ij}=0$ within W, then the assigned value $a_{ij}=0$ at 250. The time windowing and logic assignment ensures the synchronization of simultaneous pacing locations at all leads with different select logic schemes. Logic fusion rules are applied on $a_{ij}$ to determine the presence or absence of pacing artifacts. The fusion rule is a function of $a_{ij}$ i.e., $g(a_{11}, \ldots, a_{ij}, \ldots, a_{m2}) \in (0,1)$ where logic 1 or logic 0 indicate the presence or absence of pacing artifact respectively. As an example, the logical fusion rule $g(a_{11}, \ldots, a_{ij}, \ldots, a_{m2})$ to determine pacing artifacts may be voting schemes such as be majority voting, and threshold crossing (p out of 2m), combination of logical function rules such as AND, OR, etc., and Bayesian detection rules. Then, a measure of body acceleration as function of y(n) is obtained and compared with threshold $C_m$, such that $K=(f(y(n))<C_m)$, where $K \in (0, 1)$ and y(n) is the digital accelerometer signal. The final decision on the presence or absence of pacing artifact is given by $Z=K. g(a_{11}, \ldots, a_{ij}, \ldots, a_{m2})$ at 251.

At 260, based on the value of Z, different channels are activated. If Z=0, then no pacing artifact is detected and the ECG signals are sent to the output unit without attenuation. If Z=1, then samples corresponding to pacing artifact in the ECG signals are attenuated at the pacing attenuation system 261. The pacing attenuation system 261 relies on two categories of attenuation namely fixed rejection at 262 and variable rejection at 263 to remove the pacing artifacts in the ECG signal. The output of the rejection systems are combined to smoothen the samples after attenuation and obtain ECG signal without pacing artifact at Attenuation aggregator 264.

Figure 9A:
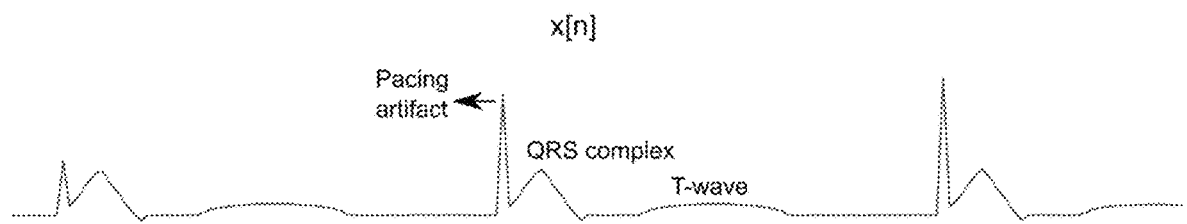
FIGS. 9A-9C show example illustrations of the pacing attenuation by fixed rejection.
Figure 9B:
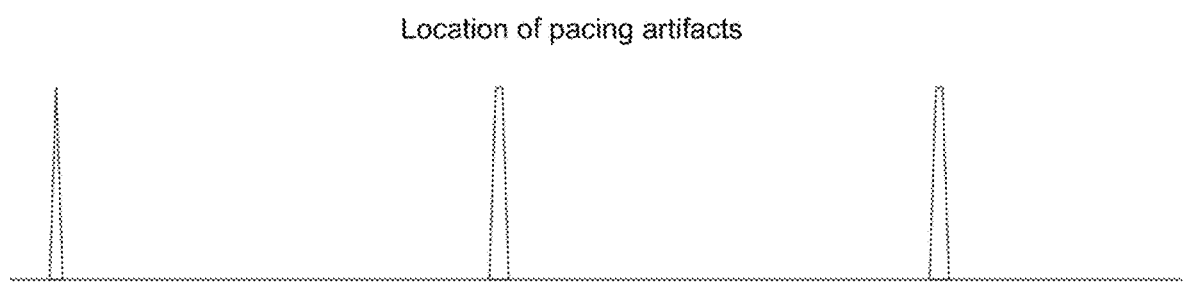
Figure 9C:
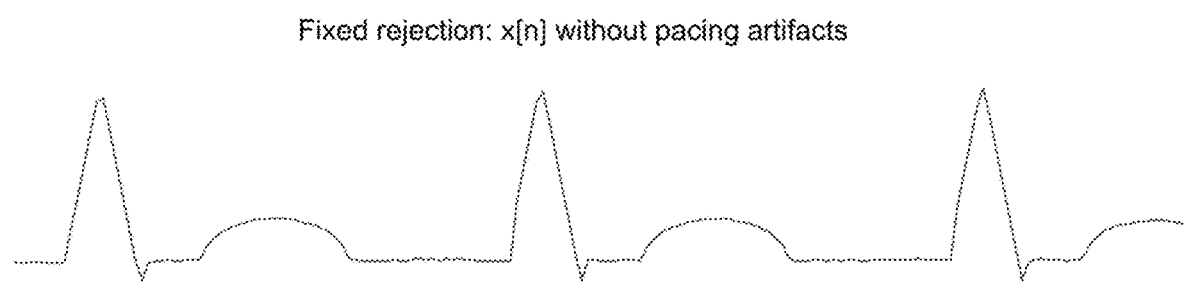

The Fixed rejection 262 system holds a constant value over the sampling instants of the pacing artifacts. As an example, if the $k^{th}$ sample is detected as a pacing sample, then the value of the $k-2^{th}$ sample may be held for k-1, k, and k+1 samples. The hold value may also be chosen to be zero to completely nullify the pacing artifacts. The duration of the hold window may be based on the sampling frequency of the recording device and pacemaker pulse width settings. FIG. 9A shows an illustration of digital ECG signal with pacing artifact and FIG. 9B shows the location of pacing artifact, where the digital stream of 1's indicate the sampling instants of the pacing artifacts. FIG. 9C shows an illustration of fixed rejection to completely remove pacing artifact where the hold value is chosen as $k-2^{th}$ sample, the hold window is given by [k-1, k+1], and k is the sampling instance.

Figure 10A:
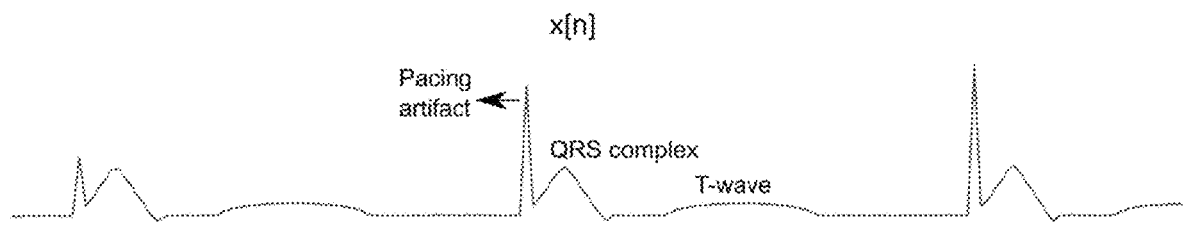
FIGS. 10A-10C show example illustrations of the pacing attenuation by variable rejection.
Figure 10B:
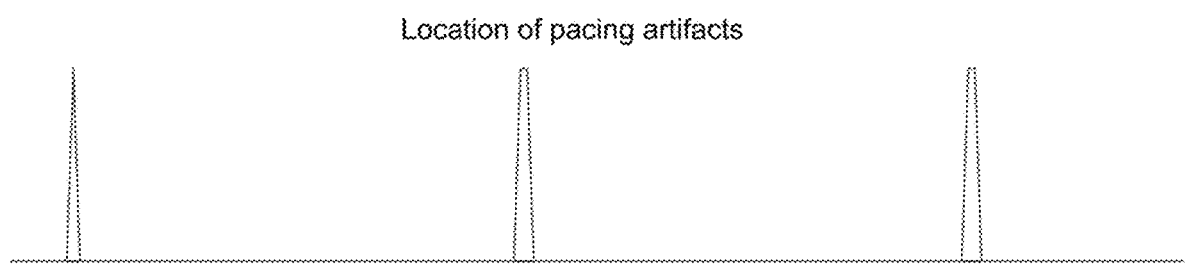
Figure 10C:
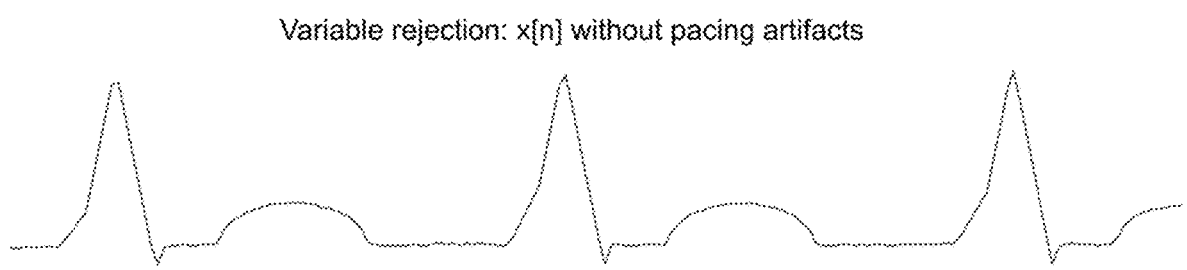

The Variable rejection 263 system creates new values over the sampling instants of the pacing artifacts thereby removing the artifact. As an example, if the $k^{th}$ sample is detected as a pacing sample, then the value of the $k-2^{th}$ and $k+2^{th}$ sample are chosen as the boundary values, and the samples between them are interpolated. The interpolation scheme may be linear, polynomial, spline, and other variants such as wavelets, rational and trigonometric interpolation. FIG. 10A shows an illustration of digital ECG signal with pacing artifact and FIG. 10B shows the location of pacing artifact, where the digital stream of 1's indicate the sampling instants of the pacing artifacts. FIG. 10C shows an illustration of variable rejection scheme where the boundary values are chosen as the $k-2^{th}$ and $k+2^{th}$ sample and the intermittent samples are linearly interpolated to reject the pacing artifacts.

Figure 11A:
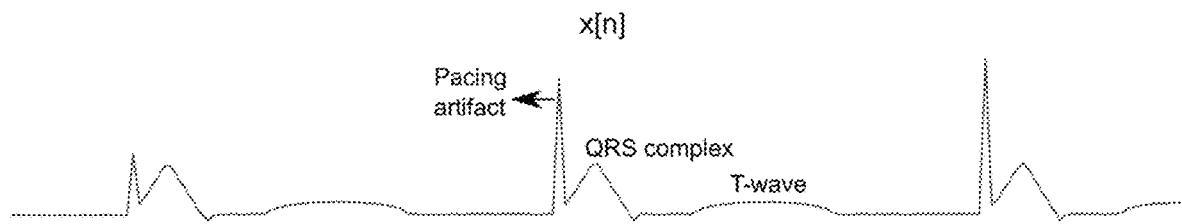
FIGS. 11A-11B show example illustrations of pacing attenuation by combination of fixed and variable rejection.
Figure 11B:
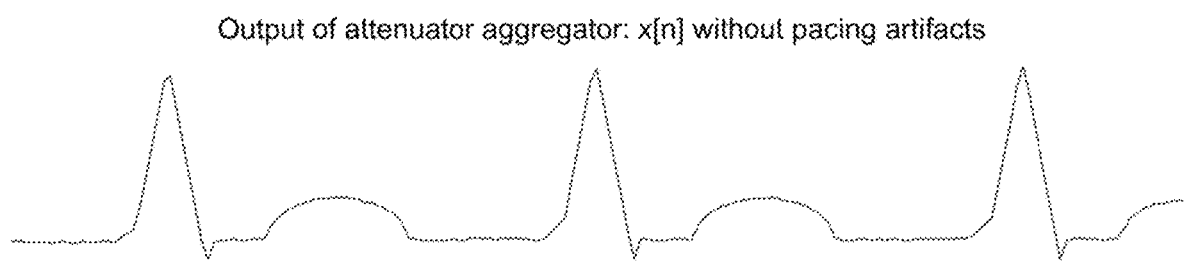

In the Attenuation aggregator 264, the outputs of the fixed and variable rejection schemes are combined to obtain the output ECG signal without pacing artifact at 265. As an example, FIG. 11A shows the digital ECG signal with the pacing artifact. FIG. 11B shows the removal of pacing artifact by taking the average of the fixed and variable rejection outputs. This step ensures the QRS morphology remains intact while smoothening the values of the samples modified due to attenuation.

It is to be noted that while combination of schemes such as direct and indirect select logic 244, 245, fixed and variable rejection 262, 263, is described in the present embodiment, they may also be standalone embodiments. Thus, the pacing artifact is removed from the ECG signal in the processing of Channel B data stream and displayed at 266.

Figure 12A:
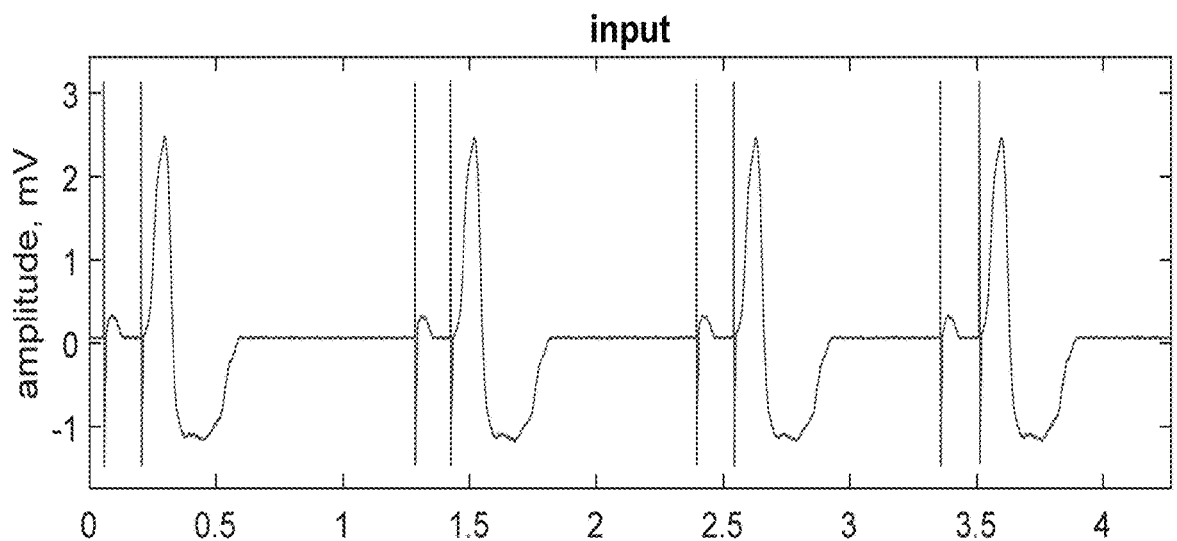
FIGS. 12A-12B show example illustrations of Illustration of synchronized overlay of pacing locations and fiducial markers (QRS complex) of ECG.
Figure 12B:
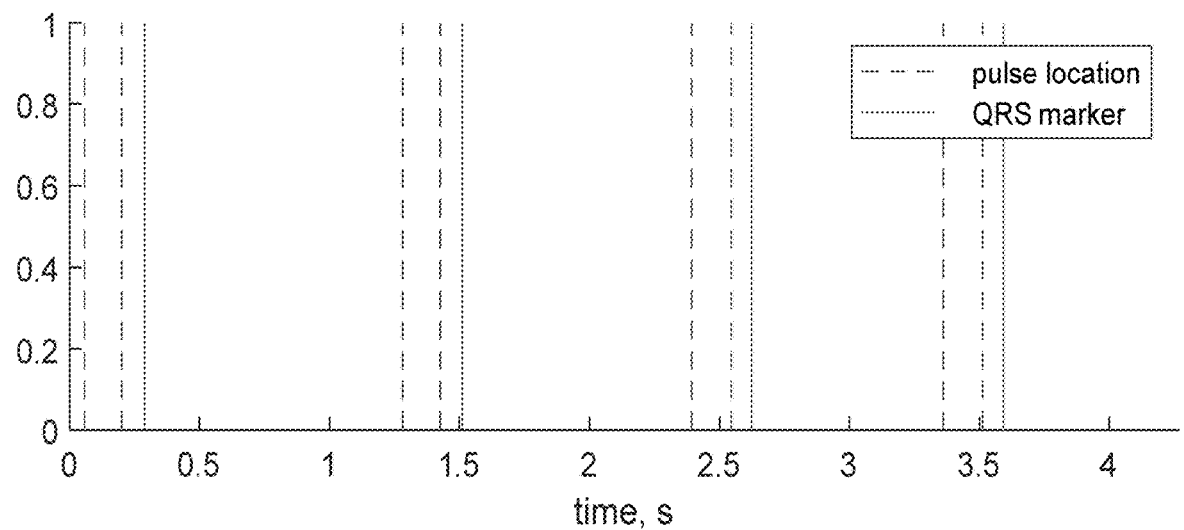

The mode and proper functioning of the pacemaker device is assessed with the aid of the outputs of Channel A and B in Paced analytics 270. The output of Channel A provides the location of pacing pulses at 236. From the output of Channel B at 265, the fiducial markers of ECG such as the peak of P wave and QRS complex are detected at 267. The locations of the pacing pulses and fiducial markers of ECG are synchronized in time and then overlaid at 268 to find the correspondence between the two streams. FIG. 12A shows the analog input ECG. FIG. 12B shows time synchronized overlay between digital pacing locations and peak marker of the QRS complex of ECG.

An example for automatic determination of the functioning and mode of the pacemaker using time synchronized overlay 268 is as follows. First, a window of duration D is applied after and before the pacing locations 236 and fiducial marker of ECG 267 respectively to determine the presence or absence of an ordered pair of PM (pacemaker pulse) and BM (beat marker such as peak of QRS or P wave). The correspondence R from PM to BM is a set of ordered pairs (pm, bm) consisting of elements pm∈PM and bm∈BM at 269. Further, at 269, the automatic determination of the normal functioning and mode is determined based on the different types of correspondences such as injective, bijective, and surjective between PM and BM, while pacemaker malfunctioning is identified by non-correspondence (i.e., there are elements in domain of function without corresponding elements in co-domain of the function).

Figure 13A:
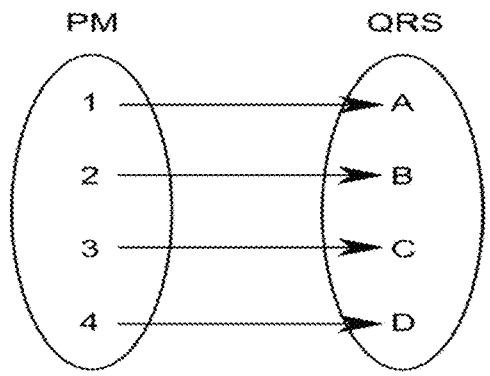
FIGS. 13A-13D show example illustrations of Illustration of correspondence measures to determine pacemaker mode and functioning.
Figure 13B:
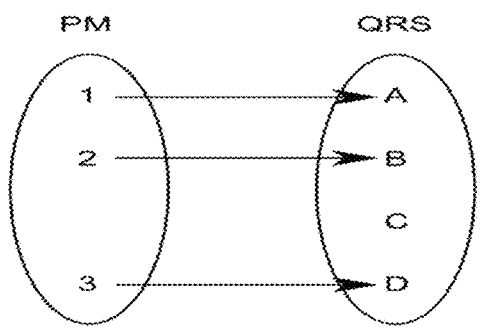
Figure 13C:
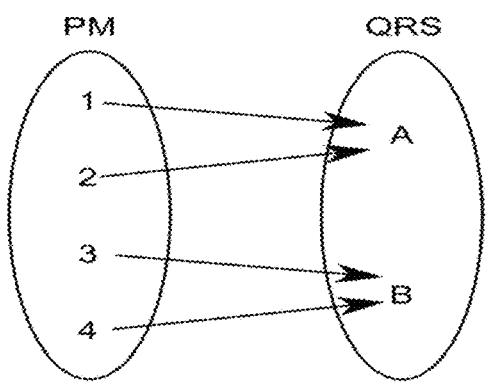
Figure 13D:
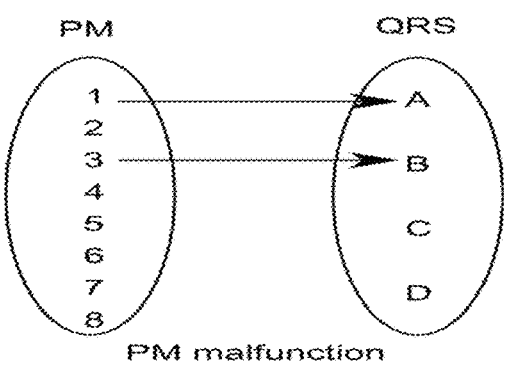

FIGS. 13A-13D shows examples of utilizing correspondence measures 269 between PM and QRS BM to determine pacemaker mode and functioning among different use cases at 271. FIG. 13A shows in one use case, the correspondence is bijective i.e., there is a one-to-one correspondence between the elements of domain PM and codomain QRS indicating normal functioning of single chamber pacing, where all beats are driven by the pacemaker. FIG. 13B shows in another use case, each element of the codomain (QRS) is mapped to at most one element of the domain PM (injective, non-surjective) indicating normal functioning of single chamber pacing, where 2 beats are driven by the pacemaker and 1 beat is an intrinsic (native) beat. FIG. 13C shows in yet another use case, each element of the codomain QRS is mapped to two elements of the domain PM indicating normal functioning of biventricular pacing, where all beats are driven by the pacemaker. Finally, as shown in FIG. 13D, when there are elements in domain of function PM without corresponding elements in co-domain of the function QRS, it indicates malfunction of the pacemaker. Combinations of the above scheme can be used to identify other functioning and modes such as ventricular capture, native beat, fusion beat, pseudofusion beat, failure to capture, undersensing, atrial pacing, ventricular pacing, and biventricular pacing, which are within the scope of the present invention.

Figure 14:
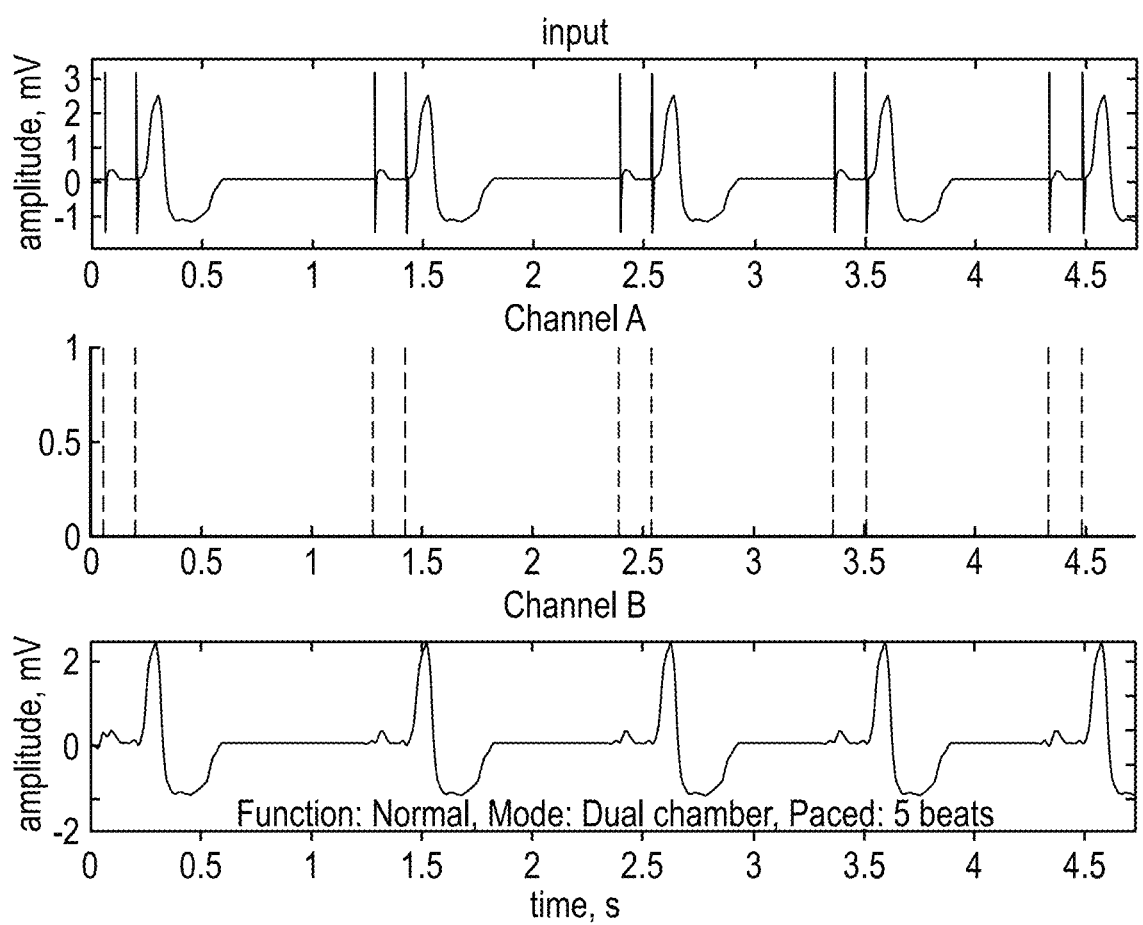
FIG. 14 shows example illustrations of paced analytics with the outputs of Channel A and Channel B data streams.

FIG. 14 shows an example of paced analytics using synchronized Channel A and Channel B data streams is provided. Thus, the pacemaker functioning and mode can be determined from diagnostic grade ECG at low sampling frequencies.

Figure 15:
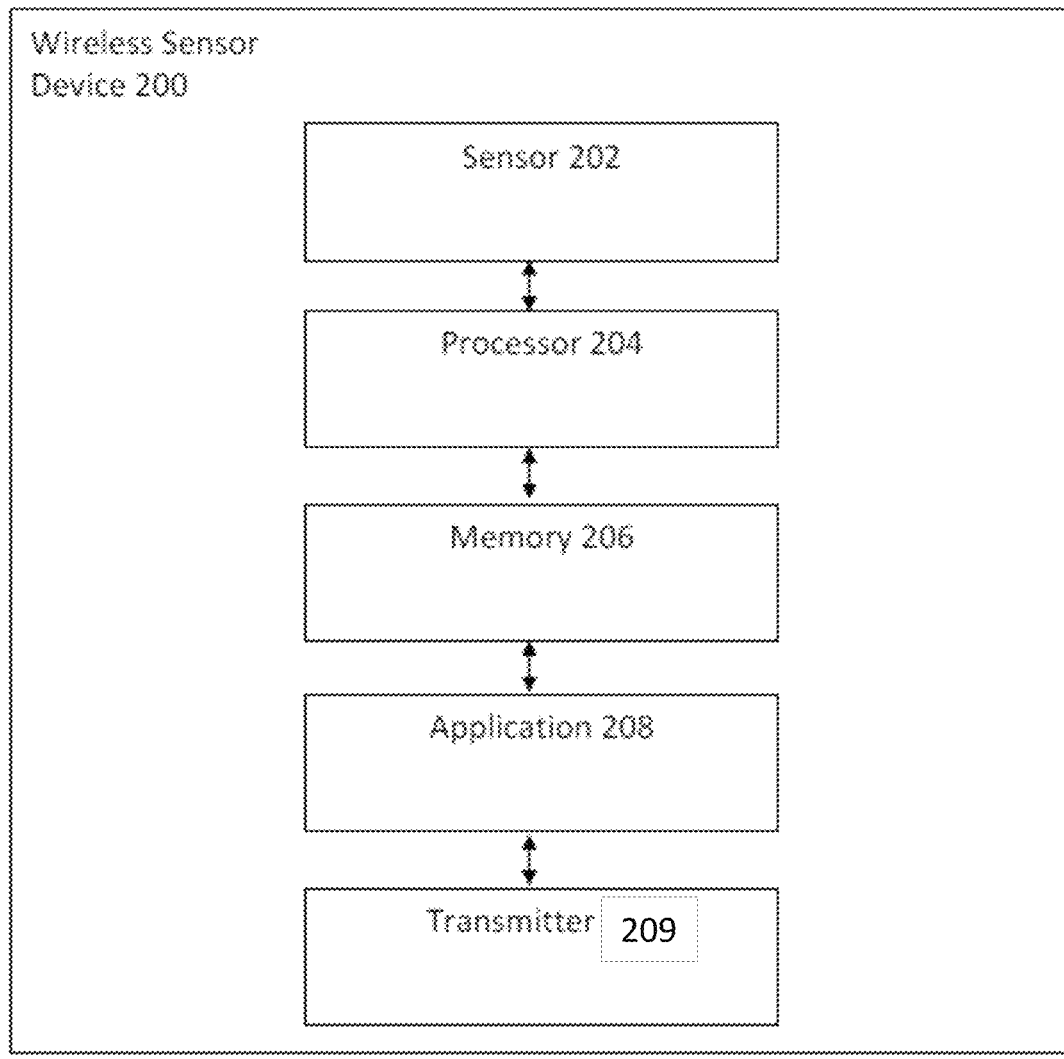
FIG. 15 shows an example illustration of a wireless and wearable sensor device 200 in accordance with an embodiment for pacing pulse indication.

FIG. 15 illustrates a wireless and wearable sensor device 200 in accordance with an embodiment. The wireless sensor device 200 includes a sensor 202, a processor 204 coupled to the sensor 202, a memory 206 coupled to the processor 204, an application 208 coupled to the memory 206, and a transmitter 209 coupled to the application 208. The wireless sensor device 200 is attached, in any orientation, to a user. The sensor 202 obtains data from the user and transmits the data to the memory 206 and in turn to the application 208. The processor 204 executes the application 208 to determine information regarding an ECG and ACC of the user and to subsequently utilize fusion of pacer detection outputs and pacemaker artifact rejected ECG outputs to determine the functional characterization of the pacemaker including pacer mode, pacer rate, pacer timing, pacing incidence, effective and ineffective pacing or pacer malfunction. The information is transmitted to the transmitter 209 and in turn relayed to another user or device.

One of ordinary skill in the art readily recognizes that the wireless and wearable sensor device 200 can utilize a variety of devices for the sensor 202 including but not limited to uni-axial accelerometers, bi-axial accelerometers, tri-axial accelerometers, gyroscopes, pressure sensors, photoplethysmograph (pulse oximeter sensors), and electrodes and that would be within the spirit and scope of the present invention. One of ordinary skill in the art readily recognizes that the wireless sensor device 200 can utilize a variety of devices for the processor 204 including but not limited to microprocessors, controllers, and microcontrollers and that would be within the spirit and scope of the present invention. In addition, one of ordinary skill in the art readily recognizes that a variety of devices can be utilized for the memory 206, the application 208, and the transmitter 209 and that would be within the spirit and scope of the present invention.

One of ordinary skill in the art readily recognizes that the information regarding an ECG of the user can be different types of information including but not limited to an ECG data signal segment and that would be within the spirit and scope of the present invention. Additionally, one of ordinary skill in the art readily recognizes that the ECG data signal segment can be measured at a variety of sampling frequencies and predetermined time periods including but not limited to a 125 Hz sampling frequency (Fs) and a predetermined time period length of 40 seconds and that would be within the spirit and scope of the present invention.

With regard to the components, results, diagrams, outputs, graphs, and operations depicted in and described in accordance with FIGS. 1-15, any of the operations and sub-operations of identifying the location of pacing pulses in diagnostic grade ECG at low sampling frequencies, attenuating the pacing artifacts in ECG, and evaluating the mode and functioning of a pacemaker device may be implemented as non-transitory computer-readable instructions stored on a computer-readable medium. The computer-readable instructions may, for example, be executed by the one or more processors of a wireless and wearable sensor, as referenced herein, having a network element and/or any other device corresponding thereto, particularly as applicable to the applications and/or programs described above.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method to assess pacemaker modes and function, comprising:
   measuring, by a wearable sensor, an analog electrocardiogram (ECG) signal;
   measuring, by the wearable sensor, an analog accelerometer (ACC) signal;
   processing, by the wearable sensor, the analog ECG signal in a first channel and providing a first channel output;
   processing, by the wearable sensor, the analog ECG signal and the ACC signal in a second channel and providing a second channel output; and
   assessing, by the wearable sensor, a mode and function of a pacemaker device using correspondence measures between the first channel output and the second channel output;
   wherein the processing the ECG signal includes extracting energy of pacing pulses using filters tuned to capture spectral content outside ECG frequencies of interest from the ECG signal.

2. The method of claim 1, wherein the processing the ECG signal further includes scaling the energy of the pacing signal in time.

3. The method of claim 2, wherein the processing the ECG signal further includes sampling the scaled pacing signal with an analog to digital converter (ADC) at a low sampling frequency.

4. The method of claim 3, wherein the processing the ECG signal further includes detecting pacing pulses from the sampled pacing signal and providing the first channel output based on the detected pacing pulses.

5. The method of claim 4, wherein the assessing the mode and function of the pacemaker device includes providing pacing pulse locations based on the detected pacing pulses of the first channel output.

6. The method of claim 1, wherein the processing the analog ECG signal and the analog ACC signal includes sampling the analog ECG signal with an analog-to-digital converter (ADC) at a same sampling frequency as the first channel.

7. The method of claim 1, wherein the processing the analog ECG signal and the analog ACC signal includes sampling the analog ECG signal with an analog-to-digital converter (ADC) in a similar range of sampling frequency as the first channel.

8. The method of claim 6, wherein the processing the analog ECG signal and the analog ACC signal further includes digitally converting the analog ACC signals by the ADC.

9. The method of claim 8, wherein the processing the analog ECG signal and the analog ACC signal further includes detecting pacing artifacts based on a combination of the sampled ECG signal and the digital ACC signal.

10. The method of claim 9, wherein the detecting pacing artifacts are detected in one or more independent leads of digital ECG based on features extracted from each lead of ECG data.

11. The method of claim 10, wherein the processing the analog ECG signal and the analog ACC signal further includes aggregating the detected pacing artifacts of the individual leads.

12. The method of claim 11, wherein the processing the analog ECG signal and the analog ACC signal further includes determining a presence or absence of the detected pacing artifact based on a measure of body acceleration derived from the digital ACC signal.

13. The method of claim 12, wherein the processing the analog ECG signal and the analog ACC signal further includes attenuating the present pacing artifacts in one or more ECG leads and providing the digital ECG signal without the pacing artifacts.

14. The method of claim 1, wherein the assessing the mode and function of the pacemaker device includes detecting fiducial markers of a digital ECG signal including a peak of P wave and QRS complex from the output of the second channel.

15. The method of claim 14, wherein locations of pacing pulses and the fiducial markers of the digital ECG signal are synchronized in time and then overlaid to find a correspondence between the first channel output and the second channel output.

16. The method of claim 15, wherein the assessing the mode and function of the pacemaker device further includes applying a window of duration D after and before the pacing pulse locations and the fiducial markers of the digital ECG respectively to determine the presence or absence of an ordered pair of pacemaker pulse (PM) and beat marker (BM), the BM including a peak of QRS or P wave.

17. The method of claim 16, wherein the assessing the mode and function of the pacemaker device further includes determining a normal functioning and mode based on different types of correspondences including injective, bijective, and surjective between the PM and the BM, and the pacemaker malfunctioning is identified by non-correspondence, wherein the non-correspondence includes elements in domain of function without corresponding elements in co-domain of the function.

18. A wireless sensor to assess pacemaker modes and function, comprising:
measuring, by an electrode, an analog electrocardiogram (ECG) signal;
measuring, by an accelerometer sensor, an analog accelerometer (ACC) signal;
processing, by a processor, the analog ECG signal in a first channel and providing a first channel output;
processing, by the processor, the analog ECG signal and the ACC signal in a second channel and providing a second channel output; and
assessing, by the processor, a mode and function of a pacemaker device using correspondence measures between the first channel output and the second channel output;
wherein the processing the ECG signal includes extracting energy of pacing pulses using filters tuned to capture spectral content outside ECG frequencies of interest from the ECG signal.

19. A non-transitory computer-readable medium, associated with a wireless sensor to assess pacemaker modes and function, storing instructions that, when executed, cause one or more processors to perform operations comprising:
measuring an analog electrocardiogram (ECG) signal;
measuring an analog accelerometer (ACC) signal;
processing the analog ECG signal in a first channel and providing a first channel output;
processing the analog ECG signal and the ACC signal in a second channel and providing a second channel output; and
assessing a mode and function of a pacemaker device using correspondence measures between the first channel output and the second channel output;
wherein the assessing the mode and function of the pacemaker device includes detecting fiducial markers of a digital ECG signal including a peak of P wave and QRS complex from the output of the second channel.

* * * * *